US010265227B2

(12) United States Patent
Wen et al.

(10) Patent No.: US 10,265,227 B2
(45) Date of Patent: Apr. 23, 2019

(54) MOBILE HUMAN-FRIENDLY ASSISTIVE ROBOT

(71) Applicant: Rensselaer Polytechnic Institute, Troy, NY (US)

(72) Inventors: John T. Wen, Melrose, NY (US); Jonas Braasch, Latham, NY (US); Utkarsh Sinha, San Jose, CA (US); Andrew Cunningham, Voorheesville, NY (US); William H. Keddy-Hector, Saratoga Springs, NY (US); Daniel C. Kruse, Troy, NY (US); David Whalen, Scotia, NY (US); Lu Lu, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 216 days.

(21) Appl. No.: 15/127,946

(22) PCT Filed: Mar. 20, 2015

(86) PCT No.: PCT/US2015/021672
§ 371 (c)(1),
(2) Date: Sep. 21, 2016

(87) PCT Pub. No.: WO2015/143273
PCT Pub. Date: Sep. 24, 2015

(65) Prior Publication Data
US 2017/0095382 A1    Apr. 6, 2017

Related U.S. Application Data

(60) Provisional application No. 61/968,826, filed on Mar. 21, 2014.

(51) Int. Cl.
*A61G 5/04* (2013.01)
*G06F 19/00* (2018.01)
(Continued)

(52) U.S. Cl.
CPC .......... *A61G 5/04* (2013.01); *B25J 5/007* (2013.01); *B25J 9/0084* (2013.01); *B25J 9/0087* (2013.01);
(Continued)

(58) Field of Classification Search
CPC .......... A61G 5/04; A61G 5/047; A61G 5/048; A61G 2203/14; A61G 2203/18;
(Continued)

(56) References Cited

U.S. PATENT DOCUMENTS

| 4,407,393 A | 10/1983 | Youdin et al. |
| 4,840,634 A | 6/1989 | Muller et al. |

(Continued)

FOREIGN PATENT DOCUMENTS

WO    9417964    8/1994

OTHER PUBLICATIONS

Begum et al., "Performance of Daily Activities by Older Adults with Dementia: The Role of an Assistive Robot," IEEE International Conference on Rehabilitation Robotics:[proceedings], Jun. 24-26, 2013.

(Continued)

*Primary Examiner* — Dalena Tran
(74) *Attorney, Agent, or Firm* — Murtha Cullina LLP; Anthony P. Gangemi

(57) ABSTRACT

A robotic assistant, associated software and methodology for operating the same. The described robotic assistant includes: a motorized base having at least two motor driven wheels controlled by a first control platform; a dual arm robot mounted on the motorized base, the dual arm robot having a first arm and a second arm controlled by a second control platform; a remote sip and puff mouth controller having three degrees of operational freedom; and a computer system that receives command signals from the remote sip and (Continued)

puff mouth controller, and includes an algorithm that translates the command signals into a first type of control signal for directing the motorized base to move, and a second type of control signal for directing the dual arm robot to move.

21 Claims, 10 Drawing Sheets

(51) Int. Cl.
    *B25J 5/00*       (2006.01)
    *B25J 9/00*       (2006.01)
    *B25J 13/00*     (2006.01)
    *B25J 11/00*     (2006.01)

(52) U.S. Cl.
    CPC ............ *B25J 11/008* (2013.01); *B25J 11/009* (2013.01); *B25J 13/00* (2013.01); *G06F 19/00* (2013.01); *G06F 19/3418* (2013.01); *A61G 2203/14* (2013.01); *A61G 2203/18* (2013.01); *A61G 2203/38* (2013.01); *A61G 2203/726* (2013.01)

(58) Field of Classification Search
    CPC . A61G 2203/726; B25J 11/009; B25J 9/1697; B25J 11/008; B25J 5/007; B25J 9/0087; G05D 2201/0206; G05D 1/0276; G05D 1/0016
    USPC ............ 700/245, 253, 258, 264; 318/568.16, 318/574; 901/15
    See application file for complete search history.

(56) References Cited

U.S. PATENT DOCUMENTS

| | | | |
|---|---|---|---|
| 5,172,147 A | 12/1992 | Rockhill | |
| 7,142,945 B2 * | 11/2006 | Wang | B25J 5/007 700/245 |
| 8,497,760 B2 | 7/2013 | Whalen et al. | |
| 8,670,017 B2 * | 3/2014 | Stuart | G06F 19/321 219/137.2 |
| 2002/0064444 A1 | 5/2002 | Wunderly et al. | |
| 2002/0193908 A1 | 12/2002 | Parker et al. | |
| 2007/0095582 A1 | 5/2007 | Stuijt et al. | |
| 2008/0265821 A1 | 10/2008 | Theobald | |
| 2011/0010013 A1 | 1/2011 | Ruan et al. | |
| 2013/0046438 A1 | 2/2013 | Summer et al. | |

OTHER PUBLICATIONS

Cavallo et al., "On the design, development and experimentation of the ASTRO assistive robot integrated in smart environments," Robotics and Automation (ICRA), 2013 IEEE International Conference on. IEEE, 2013.

Choi et al., "A list of household objects for robotic retrieval prioritized by people with ALS," Rehabilitation Robotics, Jun. 23-26, 2009, ICORR 2009, IEEE International Conference on. IEEE, 2009.

Cheng-Shiu et al., "Literature Review of Wheelchair-Mounted Robotic Manipulation: User Interface and End-User Evaluation," RESNA Annual Conference 2012.

Fasola et al., "Socially Assistive Robot Exercise Coach: Motivating Older Adults to Engage in Physical Exercise," Experimental Robotics, Springer International Publishing, 2013.

Feil-Seifer et al., "Benchmarks for evaluating socially assistive robotics," Interaction Studies: Psychological Benchmarks of Human-Robot Interaction, 8(3), 423-429, Oct. 2007.

Hillman et al., "The Weston Wheelchair Mounted Assistive Robot—The Design Story," Robotica 20.2 (2002): 125-132.

Liu et al., "A Healthcare Mobile Robot with Natural Human-robot Interaction," The Hamlyn Centre, Imperial College London, 2 pages.

Nguyen et al., "EI-E: An Assistive Robot that Fetches Objects from Flat Surfaces," Robotic helpers, int. conf. on human-robot interaction, 2008.

Haigh et al., "Automatiom as Caregiver: A survey of Issues and Technologies" AAAI-02 Workshop on Automation as Caregiver: The role of Intelligent Technology in Elder Care. 2002, 39-53.

Yoshiyuki et al., "Development of the Assistive Mobile Robot System: AMOS—to aid in the daily life of the physically handicapped" Advanced Robotics 18.5, 2004, 473-496.

Neveryd, Hakan et al.; "The Swedish experience of Rehabilitation Robotics"; Certec, Division of Rehabilitation Engineering, Department of Design Sciences, Lund University; Division of Robotics, Department of Mechanical Engineering, Lund University; 1999; pp. 6.

Zollner, R. et al.; "Programming by Demonstration: Dual-Arm Manipulation Tasks for Humanoid Robots"; IEEE/RSJ Intern. Conf. on Intelligent Robots and Systems (IROS 2004); Japan; Sep. 28-Oct. 2, 2004; pp. 6.

Unknown; "6 DOF Robotic Arm"; Dfrobot Drive the Future; WayBackMachine; May 13, 2012 pp. 3; <https://web.archive.org/web/20120513090302/http://dfrobot.com/index.php?route=prodcut/product&product_id=192>.

PCT/US2015/021672; International Filing Date Mar. 20, 2015; Notification of Transmittal of the International Search Report and Written Opinion of the International Searching Authority, or the Declaration with Search Report and Written Opinion; dated Jul. 31, 2015.

* cited by examiner

MOBILE HUMAN-FRIENDLY ASSISTIVE ROBOT

TECHNICAL FIELD

The subject matter of this invention relates to mobile assistive robots, and more particularly to a dual arm mobile assistive robot devices integrated into a motorized wheelchair for assisting mobility impaired individuals.

BACKGROUND

Mobility disabled individuals usually require full-time caretakers to be present with them to help with daily activities, which can be very expensive in the long run. One approach in addressing this need is to develop a robotic assistant that could help the user perform daily chores that they are unable to perform themselves.

Despite the proliferation of industrial robots in fields such as automotive and semiconductor manufacturing, food processing, and material handling, existing robots largely operate in a teach-and-repeat mode, with limited human interaction. For less structured environments, such as in assistive living, human guidance and intervention is essential.

Current robotic solutions for mobility impaired individuals mostly consist of a single robotic arm mounted on a wheelchair, which limits its usage to simple tasks like 'pick and place'. However, these arms are usually controlled via a joystick and as a result, are not appropriate for individuals who are paralyzed from the neck down (approx. 5000 per year in US), or have limited use of their hands. Furthermore, adapting existing robots that are controllable via human guidance for mobility impaired individuals are faced with numerous economic and technological hurdles that have yet to be fully addressed by the prior art.

Research work is also being done to develop fully automated robots that can navigate and pick/place objects by themselves. However, these systems only exist in academia and are tailored for specific scenarios or workspace. As such, most such solutions could potentially be useful for mobility impaired individuals are still some ways off of being commercially available and are also very expensive. Accordingly, a need exists for a robotic assistant that can help severely handicapped individuals.

SUMMARY

The present disclosure describes a robotic assistant that is more versatile, cheaper, and which can be remotely controllable by anyone whose mobility is impaired. The disclosed robotic assistant generally comprises a motorized base and dual arm robot mounted thereon. The robotic assistant is designed to be utilized by mobility impaired individuals through a sip-and-blow interface, tongue command device, eye/blink tracker, a joystick, etc., to, e.g., command the motion of the assistant to pick up objects from floor or shelf, to inspect suspicious noise, etc.

The assistive robot can also serve as a surrogate for medical staff/caregivers at a remote location, e.g., via the Internet, to inspect and examine the individual through vision and touch (with possible haptic feedback) and deployment of different biometric sensors such as thermometer, stethoscope, oximetry, ophthalmoscope, etc.

Sensors (e.g., vision, proximity, touch) on the robotic assistant may be used to provide feedback to the user to facilitate task execution (e.g., warning signal for impending collision, etc.). The multi-arm feature of the platform may also be used in a social companion/assistant context, to encourage exercise, play games, etc. The platform may be connected to the Internet to allow remote operation by medical staff/caregivers to inspect/examine/interact with a patient from remote surroundings. Through the distributed software architecture, the platform may be integrated into sensors/actuators in the user environment (e.g., a smart home) as a mobile sensor for home lighting, HVAC, and security systems.

The described embodiments have advantages over existing solutions, including:

(1) The multi-arm capability allows a wider range of tasks to be performed such as handling large and bulky objects, manipulating flexible objects such as clothing, cables and sheets, and inherent two arm tasks such as opening jars, preparing food, etc.

(2) The interface is adapted to handle a suite of input devices, such as mouth controllers, joysticks, etc., accessible to anybody who is mobility impaired.

(3) The robotic assistant can serve as a telepresence platform. Current telepresence systems do not have manipulation capabilities (let alone dual-arm). This platform can provide a much wider range of diagnostic and examination options, including touch and feel (through haptic feedback), and deployment of diagnostic devices.

(4) With the arms, this platform is anthropomorphic, allowing it to provide a social companion function. Because the system is teleoperated, the solution is an order of magnitude cheaper compared to systems that utilize fully automated robots.

A first aspect provides a robotic assistant, comprising: a motorized base having at least two motor driven wheels controlled by a first control platform; a dual arm robot mounted on the motorized base, the dual arm robot having a first arm and a second arm controlled by a second control platform; a remote sip and puff mouth controller having three degrees of operational freedom; and a computer system that receives command signals from the remote sip and puff mouth controller, and includes a control system that translates the command signals into a first type of control signal for directing the motorized base to move, and a second type of control signal for directing the dual arm robot to move.

A second aspect provides a control platform for controlling the operation of a robotic assistant, comprising: a control system that separately communicates with a motorized based and a dual arm robot mounted on the motorized base, wherein the control system implements a first type of control signal to control the motorized base, and a second type of control signal to control the dual arm robot; an input for receiving command signals from a remotely located controller, wherein the command signals include a proposed movement in a three dimensional space of an end effector associated with a selected arm of the dual arm robot; and a software algorithm that dictates the motion of the motorized base and dual arm robot based on the proposed movement, wherein the software algorithm only instructs the motorized base to move when the selected arm is outside a defined workspace, and only instructs the selected arm to move when the motorized base is stationary.

A third aspect provides a robotic assistant, comprising: a motorized base having at least two motor driven wheels controlled by a first control platform; a dual arm robot mounted on the motorized base, the dual arm robot having a first arm and a second arm controlled by a second control platform; an input for receiving signals from a remotely located controller, the remotely located controller having three degrees of operational input for providing a proposed movement of the robotic assistant; and a control system that separately communicates with the motorized based and dual arm robot, wherein the control system implements a first type of control signal to control the motorized base, and a second type of control signal to control the dual arm robot, and wherein the control system includes a software algorithm that dictates the motion of the motorized base and dual arm robot based on the proposed movement, wherein the software algorithm only instructs the motorized base to move when a selected arm is outside a defined workspace, and only instructs the selected arm to move when the motorized base is stationary.

BRIEF DESCRIPTION OF THE DRAWINGS

These and other features of this invention will be more readily understood from the following detailed description of the various aspects of the invention taken in conjunction with the accompanying drawings in which.

Figure 1:
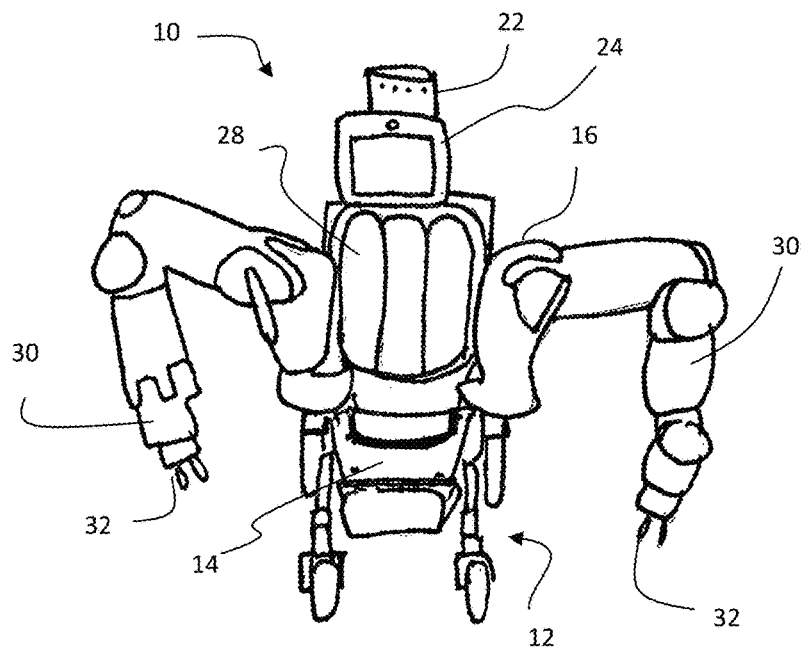
FIG. 1 shows a front view of a robotic assistant according to embodiments.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Figure 2:
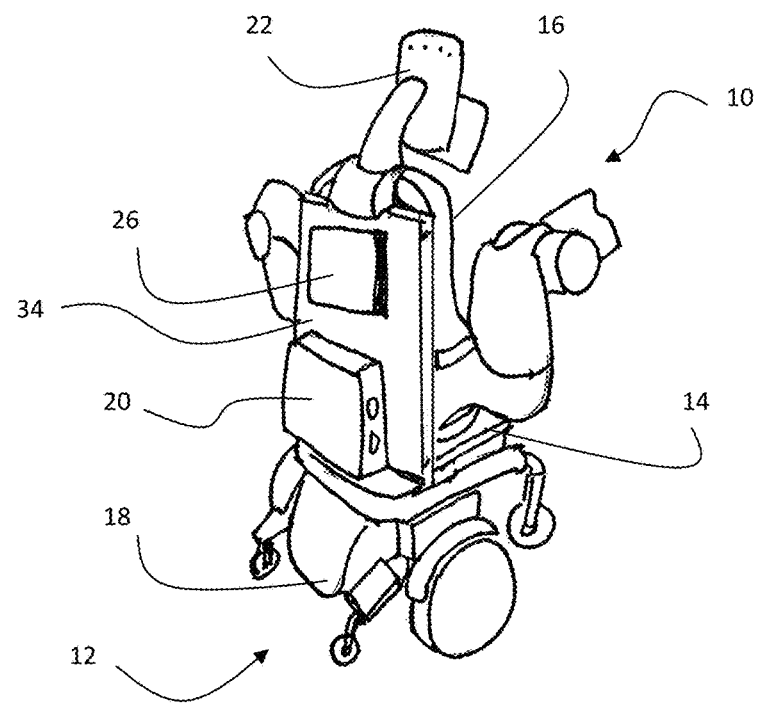
FIG. 2 shows a rear isometric view of the holder according to embodiments.

Referring now to the drawings, FIG. 1 depicts a front view and FIG. 2 depicts rear isometric view of a mobile assistive robot (hereinafter "robot" or "robotic assistant") 10 that can be remotely controlled, e.g., by mobility disabled individuals to improve their quality of life. Recent research efforts in the field of manipulation-based assistive robotics are centered on creating autonomous robotic assistants. In contrast to this common paradigm, the present approach focuses on providing a platform for allowing a handicapped individual to manually control the robotic assistant 10. Namely, a platform is provided so that the mobility disabled person is also able to control the robotic assistant 10 using an interface in order to increase the individual's independence and to maximize the number of tasks the robotic assistant 10 can complete.

Robotic assistant 10 generally comprises a motorized base 12 with at least two independently driven wheels and at least two additional small caster wheels for balance, an on-board manipulator that generally comprises a dual arm robot 16 sensors, a distributed control platform and/or other input/output devices. Robotic assistant 10 is controlled by a remote a human input device such as mouth controller, joystick, or other device.

In one embodiment, the robotic assistant 10 is an integration of a commercially available retrofitted power wheelchair, and an off the shelf dual arm robotic system such as the dual arm BAXTER™ robot by Rethink Robotics™, and a JAMBOXX™ sip and puff mouth controller. The control platform is generally managed by a computing system, such as a general purpose computer (e.g., a laptop 26) or special purpose computing device. Although various embodiments are described in terms of commercially available systems, such as a retrofitted wheelchair, Baxter robot and Jamboxx device, it is understood that other commercially available systems could likewise be utilized, as well as custom built systems.

As noted, one example of a mouth controller is the Jamboxx, which utilizes a sip and puff controller with three degrees of freedom including: (i) a slider that can be shifted left and right with the mouth, (ii) the rotation of the same slider up and down, and (iii) a pressure sensor attached to the slider used as suck/puff interface (breath controller). The design focuses on high accuracy and low movement resistance so it can be used over longer periods of time. Using this device, an impaired user can control a computer with the precision of a computer mouse.

While dual arm robots are regularly used for various industrial applications, their use is primarily limited to preprogrammed repetitive tasks. The present invention draws on tools from both industrial robotics for object manipulation and handling, and social robotics, where robots provide human communication and assistance by performing more than simple repetitive tasks. To achieve this, a human-scale lightweight dual arm robot system 16, such as the Baxter robot, is utilized. Such a robotic system can safely operate in the presence of humans and utilizes a 120V power supply, which can easily integrate with the battery power supply on the mobile base through an inverter 20.

As shown in FIGS. 1 and 2, robotic assistant 10 generally includes a retrofitted power wheel chair base (i.e., motorized base) 12 that includes a motorized drive and wheels, a battery pack compartment 18, a mounting adaptor plate 14 for mounting the dual arm robot 16, and a back plate 34 for mounting equipment and accessories. The use of existing power wheelchair technology as the motorized base 12 for the robotic assistant 10 greatly reduces the cost, while providing a proven solution. The motorized base 12 may for example be retrofitted from a QUICKIE™ s646 wheelchair powered by two lead-acid batteries, which can easily be modified for computer interface and control.

Battery pack compartment 18 may utilize any type of system (e.g., lead or lithium batteries, fuel cells, etc.) for providing power to both the wheel chair base 12 and dual arm robot 16. Because the Baxter robot operates on 120V AC, an onboard inverter 20 is utilized to convert the power for the dual arm robot 16. The dual arm robot 16, such as the Baxter robot, generally includes a torso 28, left and right arms 30, grippers 32, a display screen 24, plurality of cameras (e.g., proximate the grippers 32 and screen display 24), and head sonar distance sensors 22. An onboard laptop computer 26 is provided along with additional sensors, such as infrared or the like. In addition, a positional data collector may be implemented within the motorized base 12 and laptop 26 to track the position of the robotic assistant in a space over time.

The dual armed robot 16 as shown includes a total of fourteen degrees of freedom with seven degrees of freedom in each arm 30 and is designed to be safe to operate near humans. The robotic assistant 10 as a whole is controlled by receiving remote commands from the operator to the laptop 26 mounted on the robot 10. Once a message is received, it is interpreted by the laptop 26 and sent to either the dual armed robot, if it is a manipulation command, or the wheelchair circuitry within the motorized base 12, if it is a motion command.

Figure 3:
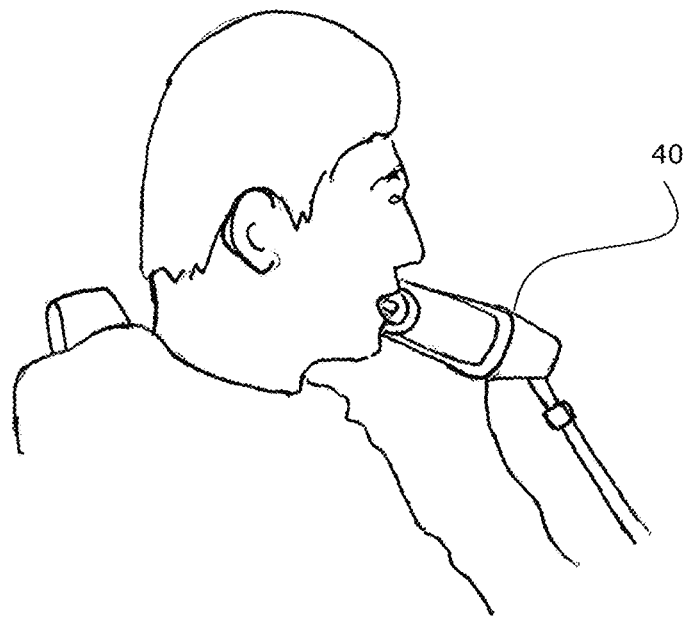
FIG. 3 shows the kinematic model of a robotic arm according to embodiments.

As noted, the Baxter robot consists of two 7-degree-of-freedom arms fixed to a rigid base, along with a suite of sensors found along the torso and on each arm. Each arm's kinematics consists of a collocated wrist, a near-collocated shoulder with a small offset between the first and second joints, and an elbow. The kinematics for the arm are shown in FIG. 3. Each joint servo is connected to an encoder and torque sensor for closed loop control and to detect servo loading from contact. Additionally, at the "end effector" of each arm is a parallel jaw gripper 32, an infrared ranger, and a camera. On the 'head' of the robot is a ring of sonar sensors 22, a display screen 24 and rotatable camera.

The internal control system for the dual arm robot 16 may be implemented with a Robot Operating System (ROS). The robot control platform subscribes to the joint positions and publishes joint velocities at a rate of 100 Hz. There are additional services running onboard the robot to prevent self-collision, publish gravity compensation torques to the servos, and, most importantly, maintain safety by halting the servos during an unexpected impact. A custom script using the Rethink Robotics Python SDK may for example be utilized to make the Baxter robot subscriptions and publications, while wrapped in a Robot Raconteur service to host the relevant joint information on a local network. This allows for rapid development in high-level languages, distribute computational effort among a network of computers, and incorporate high-performance visualizations into our control architecture.

A Jamboxx may be used as the input device to control both arms of Baxter in task space. Typically, task space controllers use Jacobian-based methods to map the end effector velocities to joint velocities. The general form of the Jacobian matrix $J_T$ is $$J_T = \begin{bmatrix} h_1 & h_2 & \ldots & h_T \\ h_1^x p_{1T} & h_2^x p_{2T} & \ldots & h_T^x p_{TT} \end{bmatrix}, \quad (1)$$

where each $h_i$ is the axis of revolution for joint i, and $p_{iT}$ is the vector from joint i to the end effector. All vectors are represented in the Baxter base frame. Each arm on Baxter has seven joints, so the Jacobian is a 6×7 matrix. The Jacobian maps between joint velocities and task spatial velocity:

$$\begin{bmatrix} \omega_T \\ v_T \end{bmatrix} = J_T \dot{q}. \quad (2)$$

Given a set of desired linear and angular velocity for the end effector, we may use the damped-least squares algorithm to command the joint motion:

$$\dot{q} = \underbrace{J_T^T (J_T J_T^T + \beta I)^{-1}}_{J_T^\dagger} \begin{bmatrix} \omega_T \\ v_T \end{bmatrix}. \quad (3)$$

Figure 4:
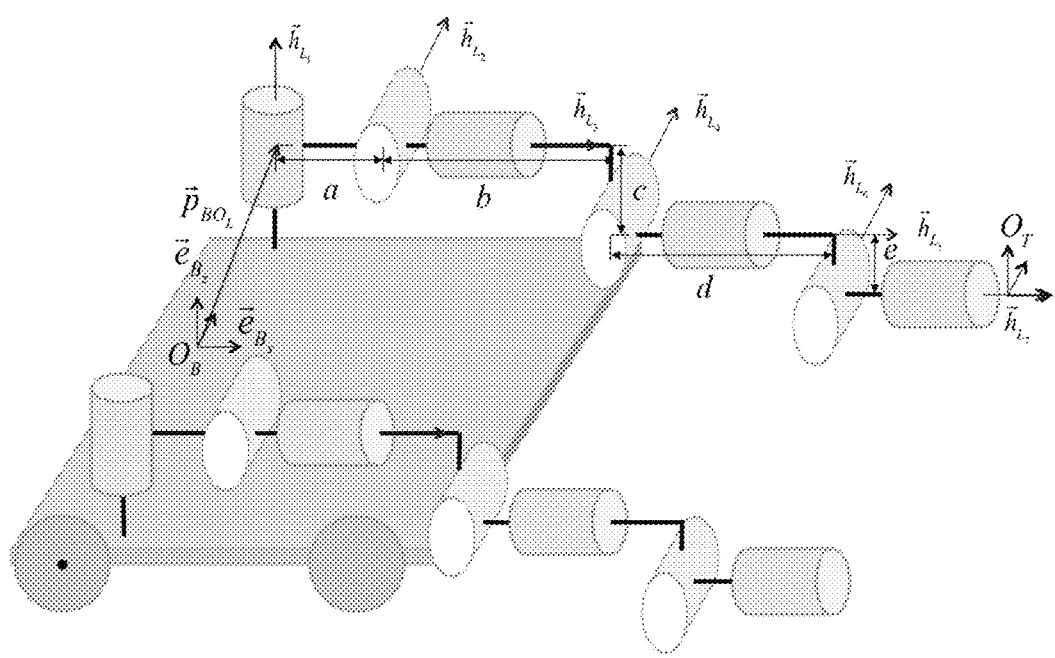
FIG. 4 shows an illustrative interface for selecting user controlled movements according to embodiments.

The coupling between position and orientation of the robot end effector may be non-intuitive for user to command. Instead, we allow the user to command position and orientation separately. The overall control consists of the following steps:

1) The user uses Jamboxx to select from a variety of options (see FIG. 4):
   Desired direction of movement for end effector (forward, backward, left, right, up, down)
   Desired wrist joint movement in the positive or negative direction
   Opening or closing of the gripper
2) The selected option is then translated into a fixed linear end effector velocity ($v_T$) or a fixed wrist joint velocity ($q_i$, for i=5, 6, or 7).
   For linear motion, the angular velocity ($w_T$) is set at zero and the damped-least squares controller is used to generate the desired joint velocity vector, which is then published to Baxter.
   For angular motion, the wrist joint velocities are directly published to Baxter.

In the described embodiment, the mobile base with batteries weighs approximately 118.8 kg while the Baxter robot weighs an additional 74.8 kg—similar to a normal adult and well within the payload range of a power wheelchair. One of the chief concerns is to ensure the safety of those around the system during use. For the mechanical design, this manifested itself into making sure that the combined system would not be in danger of tipping during normal operation. Of the possible causes for instability, the two most likely scenarios are tipping from rapid acceleration of the motorized base 12, and tipping due to center of gravity displacement. The first of these is resolved by establishing speed limits on the motorized base 12. A 'Safe' arm configuration is also chosen for rapid motion. In order to ascertain how the system's stability would be affected by the Baxter's arm movements, the center of gravity for the entire system was calculated in the most extreme possible arm configurations. A CAD model is constructed of the entire platform, complete with physical data, and used to examine the effect of arm motion on the center of gravity. It is important for the system to remain stable in all arm configurations without limiting the work envelope or payload capacity. The most effective mounting location was then chosen based on the results from these calculations. The adapter plate 14 (FIG. 1) was designed in order to locate the combined center of gravity as close to the center of the wheelbase as possible while still allowing full arm movement with the 2.3 kg max payload for which Baxter is rated.

With the chosen mounting location, the arms from Baxter have a working envelope that extends from the ground directly in front of the wheelchair to a maximum working height of 1.63 m off the ground. Each arm is also able to extend 1.04 m out to either side of the robot or 0.68 m in front of the motorized base 12. The combined footprint of an illustrative system is only 0.914 m in length and 0.673 m in width making it only 2 cm wider than the power wheelchair itself and equally as long. This is an important feature due to door and hallway width restrictions that are likely to exist in many households. In addition, a rear mounting surface 34 was designed in order to accommodate the equipment needed to mobilize the system. This provides a mounting location for the inverter 20, control laptop 26, as well as any future hardware. By locating these objects on the opposite side of the center of mass from the robotic end effecters, the stability margin was further improved particularly for the scenario when heavy objects need to be retrieved from the ground in front of the system.

There are several devices on the robot that need to be powered including the Baxter 16, laptop 26 and motorized base 12. Both the Baxter 16 and the laptop 26 are powered through a typical wall outlet while the motorized base 12 requires a 24V DC line. The power architecture is structured around the power source used in the robot: two 12V/69 Ah gel-cell batteries. The batteries are connected in series to power the mobile base 12 and in parallel to inverter 20. The inverter 20 converts the DC power into AC power that the Baxter 16 and laptop 26 can use.

Figure 5:
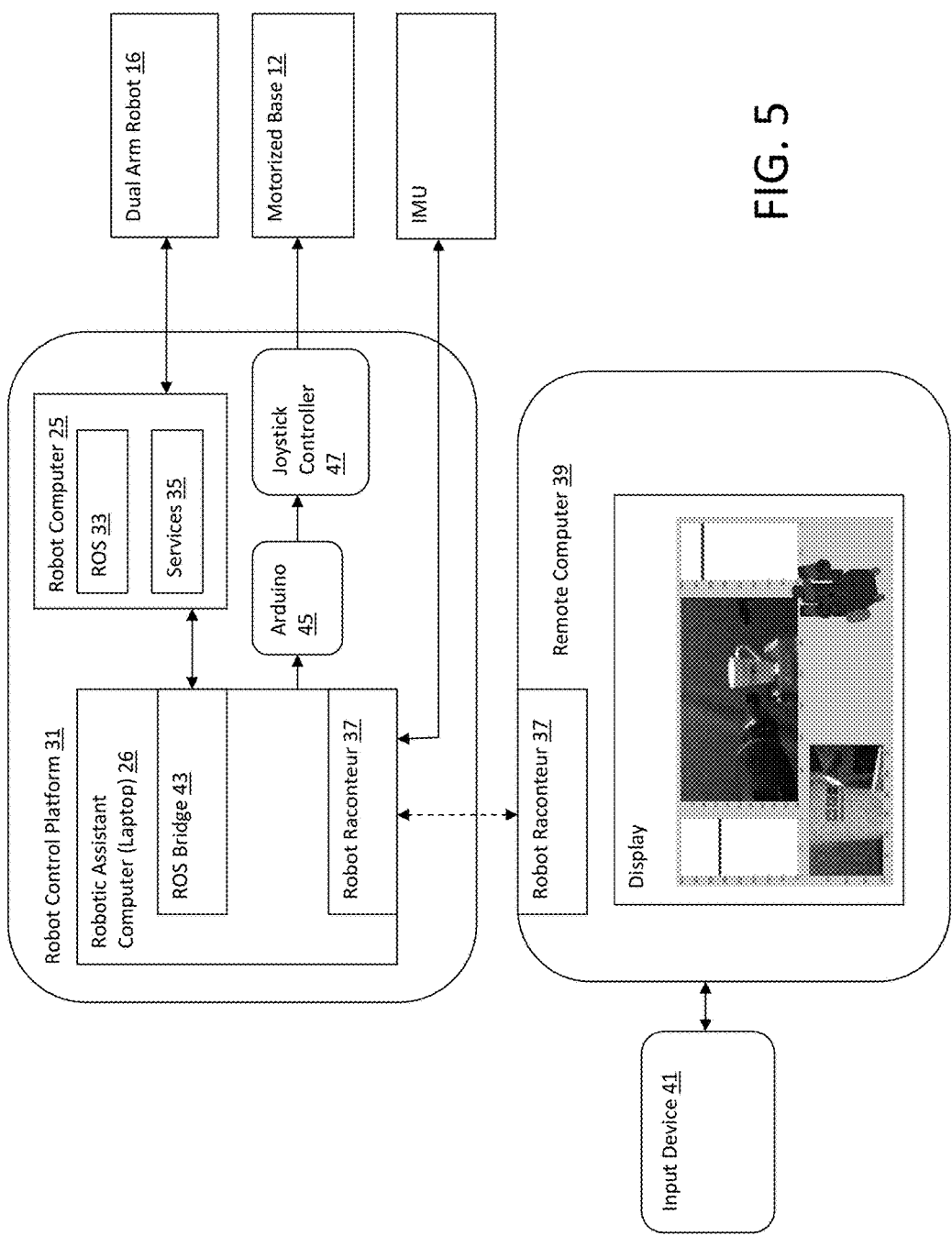
FIG. 5 shows an illustrative operational architecture according to embodiments.

Controlling the robot as a whole requires simultaneous control over both the motorized base 12 and the Baxter robot 16. To accomplish this, a laptop 26 is mounted on the rear mounting surface 34 to send the appropriate control signals to a corresponding device. When the laptop 26 receives a message from a user, it sends a command to either the Baxter 16 or the motorized base 12. The overall software architecture is shown in FIG. 5. The laptop 26 is connected to the Baxter robot 16 through Ethernet and has the capability to send commands directly to the computer inside Baxter 16. The laptop 26 receives task space commands (left, right, up, down, etc.) for moving Baxter's arms from the Jamboxx 40. It then uses a Jacobian based damped least-squares controller to calculate the joint velocities required to move the arms in the desired direction. These joint velocities are then transmitted via a custom Python script to read Robot Raconteur messages and publish ROS messages to the corresponding rostopics on Baxter's internal computer. This script acts as a Robot Raconteur ROS bridge. In contrast, the mobile base is controlled through intermediate circuitry. The laptop 26 is connected to an Arduino (via USB) which is then connected to the controller for the mobile base. When the laptop 26 receives a command to move the mobile base, it converts the command into a serial byte to send to the Arduino. Once the Arduino receives this byte, it sends a control signal to a digital potentiometer to mimic a physical joystick. This signal is passed to the mobile base's control system and functions as if it were receiving commands from a physical joystick.

Any type of input devices may be utilized to operate the robotic assistant 10, including, e.g., a Jamboxx or a joystick. Using such devices, two possible control schemes may be implemented. The first control scheme involves placing all functionality required to control the robot 10 on a single input device. This results in the ability to drive the mobile base and operate the arms at the same time with ease.

A second control scheme involves a hybrid approach and utilizes both the Jamboxx and joystick. This scheme was tailored towards for use by quadriplegics as they are able to proficiently use the Jamboxx and can often control a joystick, like the ones mounted on a wheelchair, as well. In one embodiment, Baxter is controlled by the Jamboxx while the motorized base 12 is controlled by a joystick.

In addition to the controller layout, feedback from the system is delivered to the user in two ways. First, the Baxter robot 16 itself is equipped with three onboard cameras which can stream video to the operator. There is a head camera which provides an overhead view of the motion of the system, as well as two cameras located on the end effectors of the two arms. By using a combination of the viewpoints, the operator is able to see how the robotic assistant 10 is positioned in order to complete the desired task.

Figure 6:
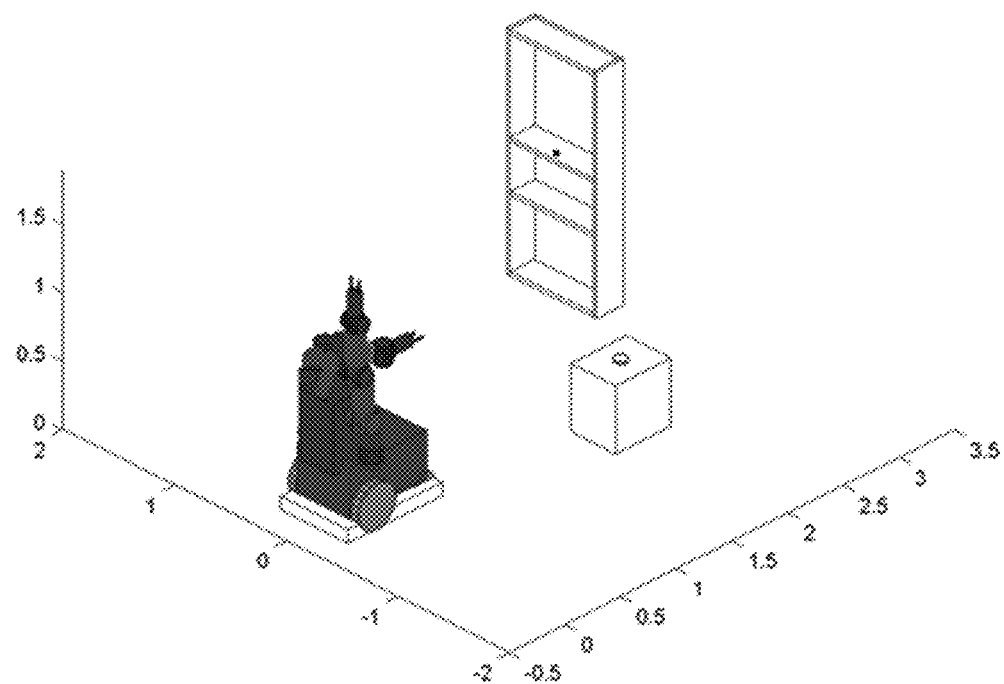
FIG. 6 shows an illustrative graphical representation of a robotic assistant according to embodiments.

A custom MATLAB simulation package may be utilize to give the operator real-time feedback of the arm positions. This may be done by approximating the joints and linkages of the robot with a set of primitive 3D shapes. By using the known forward kinematics of the system, the current arm configuration is drawn by passing the drawing package a series of joint angles for each arm. A simulated configuration is shown in FIG. 6. Having the capability to simulate the robotic system also provides the dual functionality of allowing the designers to test different control layouts, or allowing users to get comfortable operating the robotic assistant 10, without needing to activate the physical system. This will be particularly useful when individuals with different physical disabilities require custom control interfaces.

In the first control scheme noted above, both the mobile base and dual arm robot are controlled by a single input device, such as a Jamboxx. There are two typical operations: local tasks, which are within the arm workspace, and non-local tasks, which require base motion to position the task within the arm workspace. Arm and base are either controlled separately or together as an integrated unit. In the former case, the mobile base moves the arm into the area of interest and remains stationary while the arm performs the task. This requires switching between the two modes, placing added burden on the user. In the latter case, the arm and base may move together even when the base motion is unnecessary. Such unanticipated base motion compromises safety and, because of the weight of the system, reduces responsiveness and consumes more energy.

In the following embodiment, a general human-robot cooperative control approach is provided in which the system automatically determines if the mobile base needs to be moved to get an arm into a desired workspace. The arm (or arms) will only then move when the motorized base 12 is within the work space. The arm(s) thus stay stationary while the motorized base 12 moves, but the process is automated so that the user does not need to switch between the two modes.

This is achieved by providing a highly redundant mobile robotic system with the human user providing motion command through an input device with a limited number of degrees of freedom. The control problem is posed as a constrained optimization at the kinematic level that determines the robot joint velocity to minimize the deviation from the human commanded motion input. A set of equality and inequality constraints is imposed based on joint and velocity limits, singularity avoidance, and collision prevention. In addition, an equality constraint is included to ensure that the base motion follows the commanded end effector motion in a natural way by avoiding unanticipated combined arm/base motion. Since the problem is kinematic in nature, the resulting minimization becomes a convex quadratic program which guarantees a unique, and efficiently solvable, solution. This type of kinematic based algorithm is local in nature, meaning that even a globally feasible motion plan exists for the overall task, the motion may get stuck locally.

One goal is to locally follow the human command as closely as possible without violating the constraints, and rely on the human user to steer the system for the global task. A key motivation for this work is to provide assistance to severely mobility impaired individuals.

Figure 7:
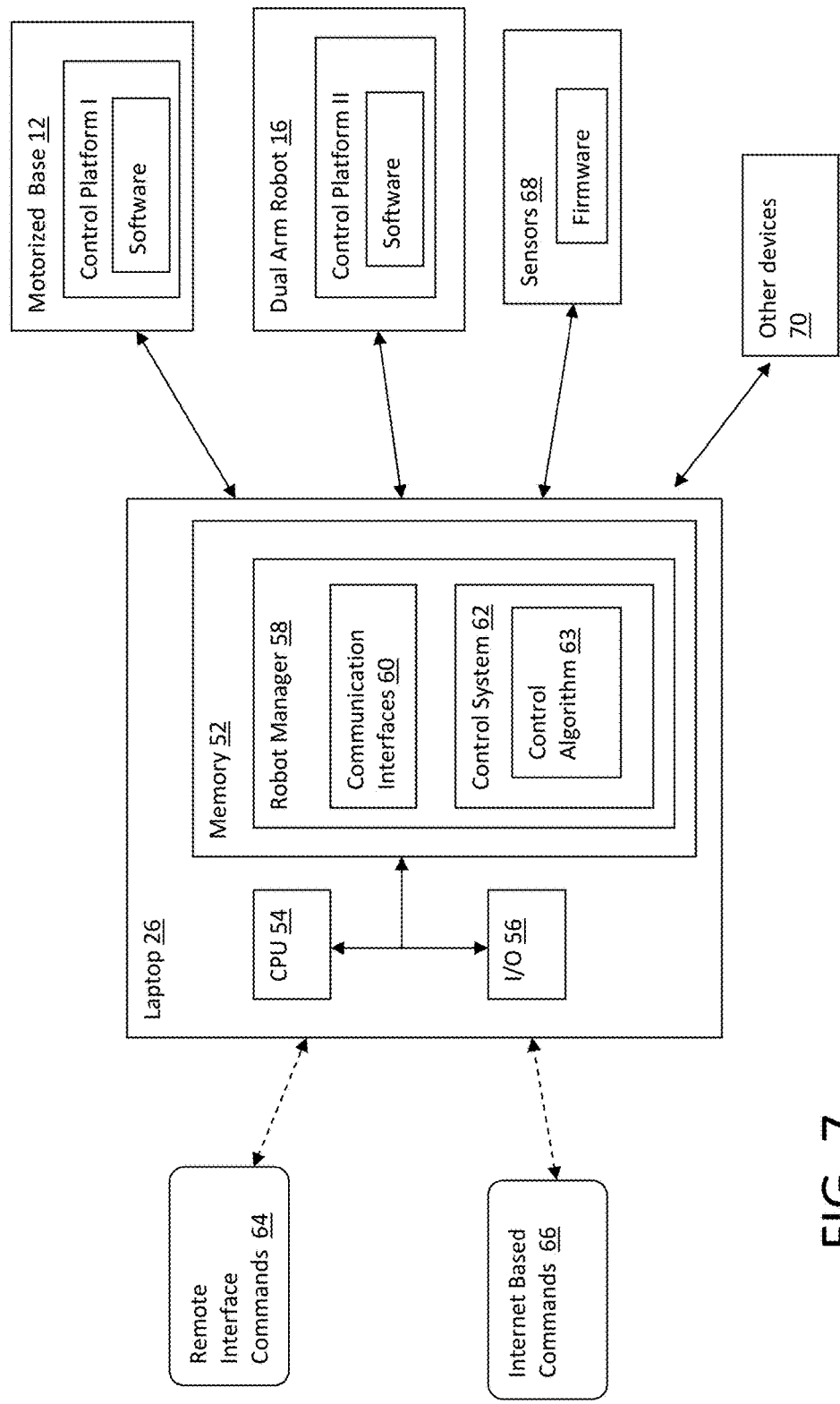
FIG. 7 shows the kinematic model of the robotic assistant according to embodiments.

FIG. 7 shows a schematics of the system at the zero configuration, where all the joint angles are at zero, and the motorized base 12 is centered at the origin and facing the positive x-direction of the inertia frame. The numerical values of the robot parameters are:

a=0.069 m; b=0.364 m; c=0.069 m; d=0.374 m e=0.01 m; $pBO_L = [0{:}004, 0{:}259, 0{:}390]^T$ m.

Only the left arm is labeled; the right arm is identical to the left, symmetrical with respect to the x-z plane of the base frame. The link parameters of the arms are a, b, c, d as shown in the diagram. The displacement of the base of the arms from the motorized base 12 coordinate center is given by the vector $pBO_L$ and $pBO_R$. The joint angles of the left and right arms are denoted by the vectors $q_L$ and $q_R$, respectively, where $q_L$ consists of $\{q_{L1}, \ldots q_{L7}\}$ and $q_R$ consists of $\{q_{R1}, \ldots q_{R7}\}$. Assume no wheel slippage, the kinematics of the motorized base 12 is given by the standard unicycle model:

$$\underbrace{\begin{bmatrix} \dot\theta_B \\ \dot x_B \\ \dot y_B \end{bmatrix}}_{\dot q_B} = \underbrace{\begin{bmatrix} 1 & 0 \\ 0 & \cos\theta_B \\ 0 & \sin\theta_B \end{bmatrix}}_{J_B} \begin{bmatrix} \omega_B \\ v_B \end{bmatrix}$$

where $(x_B, y_B)$ is the motorized base 12 center with respect to inertia frame, $\theta_B$ is the orientation of the motorized base 12, and $(w_B, v_B)$ are the turning and linear velocities of the motorized base 12. In this discussion, we only consider one arm at a time, e.g., the left arm. The differential kinematics of the left arm/base system in the mobile base frame is given by $$V_T = J_{T_L}\dot q_L + \begin{bmatrix} e_z \omega_B \\ -(p_{BO_L} + p_{O_L T_L}) \times e_z \omega_B + e_x v_B \end{bmatrix}$$

where $VT = [wT, vT]^T$ is the spatial velocity (angular and linear) of the task frame at the end effector, $J_{TL}$ is the corresponding arm Jacobian, $p_{OLTL}$ is the arm base to end-effector vector, $e_x = [1, 0, 0]^T$ and $e_z = [0, 0, 1]^T$ are the unit vectors in the base frame.

Combining these two equations, we can write the overall kinematics in a compact form:

$$V_T = J_T(q)u = \begin{bmatrix} J_{T_L} & e_z & 0 \\ & -(p_{BO_L} + p_{O_L T_L}) \times e_z & e_x \end{bmatrix} u$$

$$\dot q = J_q(q)u = \begin{bmatrix} I & 0 \\ 0 & J_B \end{bmatrix} u$$

where $$q = \begin{bmatrix} q_L \\ q_B \end{bmatrix}, u = \begin{bmatrix} \dot q_L \\ \omega_B \\ v_B \end{bmatrix}.$$

Consider the scenario where the human user provides the desired motion, in terms of either position or velocity, through an input device. The goal is to determine the mobile manipulator joint motion (including both the manipulator and the mobile base) to stay close to the human command while satisfying a set of equality and inequality constraints.

The user would typically use velocity command for large motion (the input is like a gas pedal) and position command for close-up, more precise motion. The constraints could be due to environmental constraints, singularity avoidance, or specified joint pose. There is also the more qualitative requirement (for now) that the robot motion should be "natural", avoiding unanticipated internal arm motion or the base motion.

To be more precise, denote the Euclidean frame (orientation and position) the human user is commanding by $\{E_A, O_A\}$. This could be the end effector frame or a frame affixed somewhere on the robot, e.g., the arm elbow joint or the base. The differential kinematics is given by $V_A = J_A(q)u$, where $V_A$ is the spatial velocity of frame A, $J_A$ the Jacobian, q the robot configuration (manipulator joint displacement and the base position and orientation), and u the commanded velocity (manipulator joint velocities and mobile base heading velocity and angular velocity). The user may command just a subset of frame A, e.g., translation or rotation. For the purpose of this discussion, only translation is considered, as it is the most common type of operation. Rotation may be useful in dual arm operation as well, but is omitted for brevity. Denote the corresponding linear velocity, in the mobile base frame, by $v_H$, which may be a direct velocity command from the user or the velocity control for the position command. The human-directed velocity $v_H$ is related to the $v_A$ through a selection matrix S:

$$v_H = S v_A = S J_A(q)u := J_H(q)u.$$

The user can also specify some joints or frames in the robot to be in a given configuration, e.g., elbow up or down to avoid bumping into objects, or fixed wrist orientation to hold a tray level. It is also important to observe joint limits, avoid singularities which would reduce mobility, and maintain a safe distance from obstacles. All of these are holonomic constraints on the robot configuration. To be specific, the problem that we are addressing is to determine u to best achieve the commanded velocity $v_H$ while observing imposed equality and inequality constraints:

$$\min_u \|J_H u - v_H\| \text{ subject to}$$

$$h_E(q) = 0$$

$$h_I(q) \geq \eta > 0.$$

$$\dot q = J_q(q)u, q(0) = q_0.$$

As q is dynamically related to u, this is an optimal control problem over a specified time period [0, T] (with a given $\{v_H(t): t \in [0, T]\}$), and the norm in the above formulations is a functional norm. We relax the problem by converting the equality constraint to a soft constraint (becoming part of the control objective) and the inequality constraint to a barrier function. For the equality constraint, consider a Jacobian-based velocity control:

$$v_E := J_E(q)u = -k_E h_E(q),$$

where $J_E$ is the Jacobian corresponding to $h_E(q)$ and $k_E$ is the feedback gain. If the number of equality constraints is less than the number of joint velocity input, and the robot is not at a singular configuration with respect to $J_E$, then $J_E$ is full row rank and this equation always has at least one solution.

Figure 8:
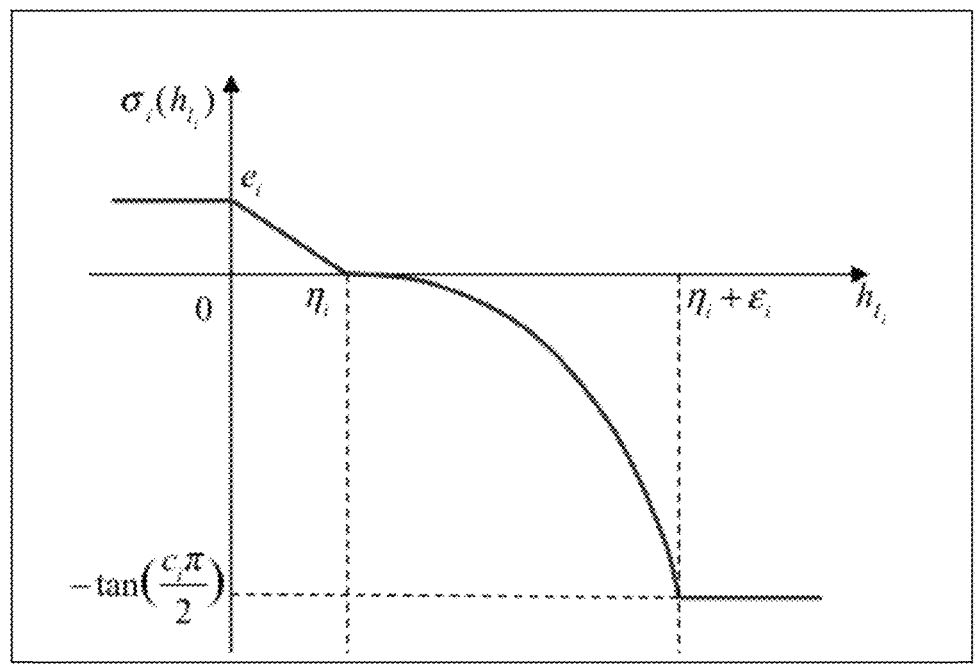
FIG. 8 depicts a graph showing inequality constraints according to embodiments.

For the inequality constraint, we require the input to steer the system towards the feasible region if it is infeasible, and remain in the feasible region if the system is already within it. This becomes a linear inequality constraint on u:

$$\frac{dh_{l_i}}{dt} = \frac{\partial h_{l_i}}{\partial q} J_q(q) u \geq \sigma_i, \, i = 1, \ldots, n_i$$

where $J_q$ is the arm Jacobian (needed for the nonholonomic base constraint), $n_i$ is the number of inequality constraints, and $\sigma_i$, shown in FIG. 8, is given by $$\sigma_i = \begin{cases} -\tan(c_i \pi/2), & \text{if } h_{l_i} \geq \eta_i + \varepsilon_i \\ -\tan(c_i \pi(h_{l_i} - \eta_i)/2\varepsilon_i) & \text{if } \eta_i < h_{l_i} < \eta_i + \varepsilon_i \\ e_i(\eta_i - h_{l_i})/\eta_i & \text{if } 0 \leq h_{l_i} \leq \eta_i \\ e_i & \text{else} \end{cases}$$

with $n_i$ specifying the region in which the velocity constraint becomes active, $e_i$ ensures that an infeasible inequality constraint is moved towards the feasible region, and $c_i < 1$ but close to 1 to avoid possible large amplitudes of $\sigma_i$. The dynamic optimal control problem now becomes a static optimization problem to determine the input u at each time instant:

$$\min_u \|J_H u - v_H\|$$

$$J_E(q) u = -K_e h_E(q)$$

$$\frac{\partial h_{l_i}}{\partial q} J_q(q) u \geq \sigma_i, \, i = 1, \ldots, n_i.$$

A regularization term $\|u\|$ may need to be added to the cost function to ensure that the solution is unique. This problem is a convex quadratic program which may be efficiently solved using commercially available tools. If a solution exists, then the robot would remain within the feasible region while staying close to the human commanded motion. However, there could be the local minimum issue when the algorithm is "stuck" (u=0 before the goal is reached). For the purposes of brevity, we only consider local solution of u and rely on the human user to steer out of local minima, if encountered.

The design of the inequality and equality constraints is critical to well coordinated motion under human command. We formulate a set of design requirements below to guide the choice of these constraints.

1) When the user does not give commands ($v_H$ is zero), both the arm and the motorized base 12 do not move. This requirement is obviously necessary to avoid any unintended surprise motion.

2) When the arm is inside the interior of the workspace, only the arm moves but not the motorized base 12. This requirement is to avoid excessive base motion when arm alone could follow the user command.

3) When the arm is at the workspace boundary, and the user commanded velocity is the direction that would move beyond the arm workspace, then the motorized base 12 should move to achieve the desired user motion commands with the end-effector orientation locked. This requirement allows base motion only when it is necessary to follow the user command.

Figure 9:
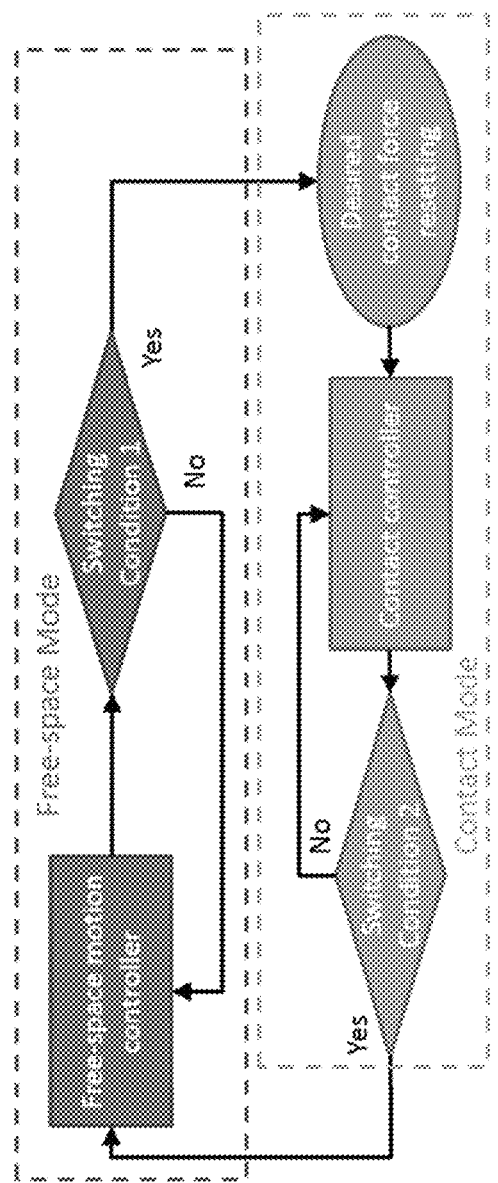
FIG. 9 shows graphical arm positions of the robotic assistant according to embodiments.

4) When the arm is at the workspace boundary, the base motion should result in the end-effector motion in the same direction as the user commanded motion. This requirement will avoid the unnatural motion where the base seems to not follow the user command (with the arm also moving to compensate for the undesired base motion). This situation is illustrated in FIG. 9 using the Jacobian pseudo-inverse controller. Note that during the transient (as in t=2.5 sec and t=5 sec snapshots), the base rotates in the opposite direction as the user commanded direction. Eventually the base rotates in the right direction, but such unnatural transient motion should be avoided.

5) When the obstacle is close to the mobile base, the mobile base speed is reduced, and eventually becomes zero as the minimum distance to the obstacle decreases. This requirement is necessary for safety.

We will refine the constrained optimization problem step-by-step to satisfy the above requirements. The first step is to remove the equality constraint through a reparameterization of u:

$$u = J_E^\perp \xi + J_E^+ v_E$$

Where the columns of $J_E^\perp$ is a basis of the null space of $J_E$ and $J_E^+$ is the Moore-Penrose pseudo-inverse of $J_E$. The previous becomes $$\min_\xi \|J_H(J_E^\perp \xi + J_E^+ v_E) - v_H\|$$

subject to $$\frac{\partial h_{l_i}}{\partial q} J_q(q)(J_E^\perp \xi + J_E^+ v_E) \geq \sigma_i, \, i = 1, \ldots, n_i.$$

If the matrix $J_H J_E^\perp$ is not of full column rank or is ill conditioned, there could be large changes in u in each iteration. One solution is to add a penalty term to prevent u to deviated too far from its previous value:

$$\min_\xi \|J_H(J_E^\perp \xi + J_E^+ v_E) - v_H\| + \lambda \|(J_E^\perp \xi + J_E^+ v_E) - u_{prev}\|$$

subject to the above, where $u_{prev}$ is the input in the previous iteration, and $\lambda$ is a weighting factor for the relative emphasis between changes in u versus following the user command. The problem with this approach is that even when the user is not moving, i.e., $v_H=0$, the robot could continue to move (violating Requirement 1). We therefore adopt an alternate approach by adding a regularization term to the cost function. Let $$J_{HE} = \begin{bmatrix} J_H \\ J_E \end{bmatrix}^\perp$$

Replacing the optimization problem above by $$\min_\xi \|J_H(J_E^\perp \xi + J_E^+ v_E) - v_H\| + \lambda \|(J_{HE}^T(J_E^\perp \xi + J_E^+ v_E))\|$$

subject to the same constraint. Since $$\begin{bmatrix} \begin{bmatrix} J_E \\ J_H \end{bmatrix} \\ J_{HE}^T \end{bmatrix}$$

is square invertible, $$\begin{bmatrix} \begin{bmatrix} J_E \\ J_H \end{bmatrix} \\ J_{HE}^T \end{bmatrix} J_E^\perp = \begin{bmatrix} 0 \\ J_H J_E^\perp \\ J_{HE}^T J_E^\perp \end{bmatrix}$$

is of full column rank. This implies $$\mathcal{N}((J_H + \lambda J_{HE}^T)J_E^\perp)^- = \{0\}$$

where N denotes the null space. Hence the minimization problem is strictly convex, meaning that there will be no unwanted motion, and at the same time, the user command tracking or motion imposed by the equality constraints are not be unduly penalized. The constant λ is again a weight constant between motion in the null space, and user command following. It is preferable to move the arm, instead of the base, whenever possible, as the arm is lighter weight and flexible, and therefore more responsive, consumes less energy, and less threatening to the user. To emphasize arm motion over base motion, we add a penalty term to the base motion. Let C be a matrix that select the base velocity command from u:

$$\begin{bmatrix} v_B \\ \omega_B \end{bmatrix} = Cu.$$

Define $$J_{HEC} = \begin{bmatrix} J_H \\ J_E \\ C \end{bmatrix}^\perp$$

Figure 10:
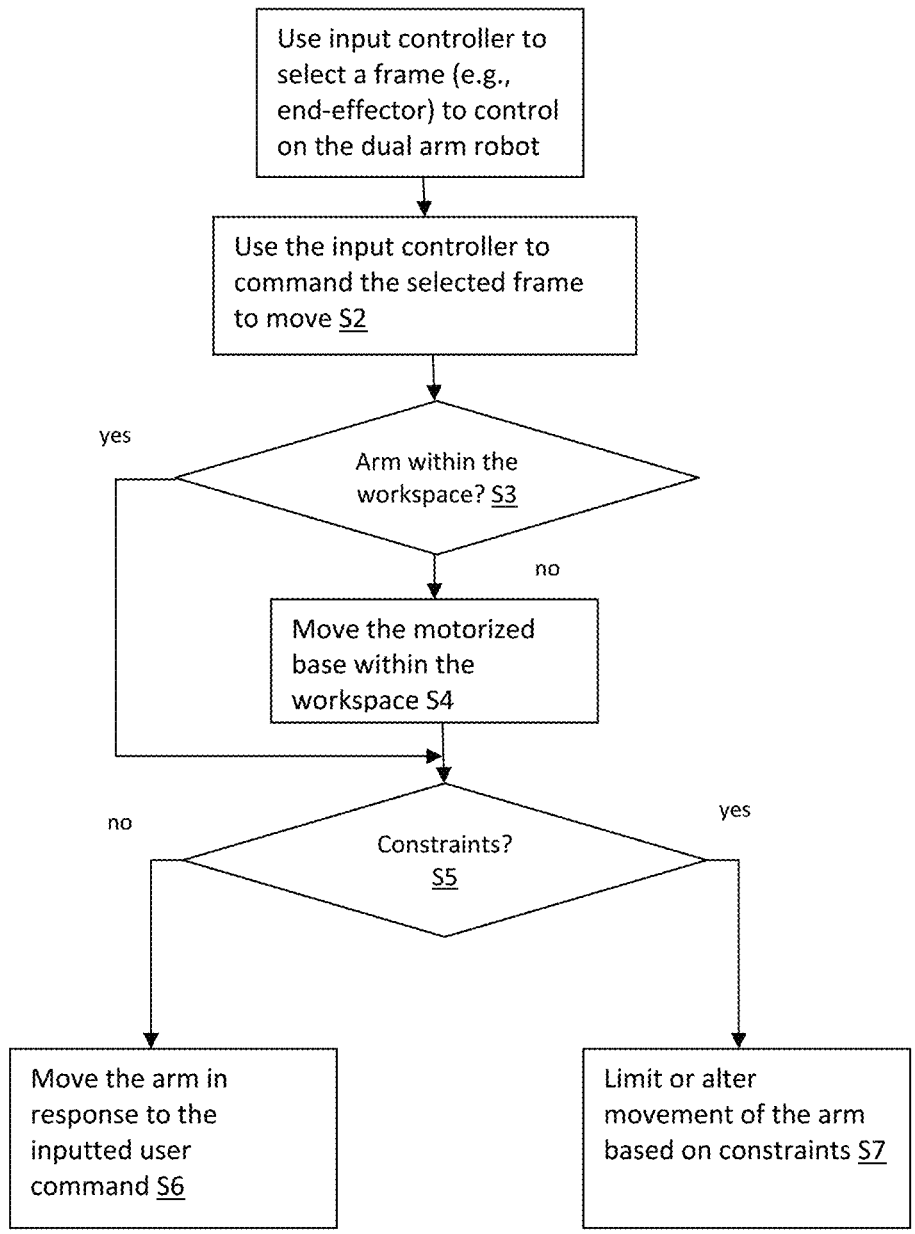
FIG. 10 shows kinematic arm motions according to embodiments.

We then replace the above by $$\min_\xi \|J_H(J_E^\perp \xi + J_E^+ v_E) - v_H\| + \lambda_1\|(J_{HEC}^T(J_E^\perp \xi + J_E^+ v_E)\| + \lambda_2\|C(J_E^\perp \xi + J_E^+ v_E)\|$$

where λ1 is the weighting for the null space motion and λ2 is the weighting for the base motion. If the user command and equality constraints may be satisfied with arm motion alone without violating the inequality constraints, this method ensures that there would be no base motion, satisfying Requirements 2 and 3. In the specific case when the user commands a fix point on the arm to translate in certain direction and the arm reaches its boundary, it is more natural to have the base follow the desired direction of motion (projected onto the x-y plane), rather than having other combined base/arm motion, as shown in FIG. 10. In this case, we add a single equality constraint $$e_z^T(v_H \times (\omega_B \times p_{OT} + v_B)) = J_{EB} u = 0$$

where $p_{OT}$ is the vector from center of the wheel axle to OT, and $J_{EB}$ is the matrix that captures the constraint. The equality constraint is only enforced in the ez direction since we are only interested in the x-y components of $v_H$. We now simply append this additional constraint to the existing equality constraint $$\underbrace{\begin{bmatrix} J_E \\ J_{EB} \end{bmatrix}}_{E} u = \underbrace{\begin{bmatrix} v_E \\ 0 \end{bmatrix}}_{\beta}.$$

This ensures that we satisfy Requirement 4. Requirement 5 follows from the inequality constraint defined above. Summarizing the above, the proposed control algorithm for the kinematic control u for a given user velocity command and equality and inequality constraints is given below:

Algorithm:

Consider a mobile manipulator at a configuration q, with the user specified velocity $v_H$, equality constraint, and inequality constraint. Choose the robot motion input u as provided above, with x solved from the following quadratic programming problem:

$$\min_\xi \|J_H(E^\perp \xi + E^+ \beta) - v_H\| + \lambda_1\|(J_D^T(E^\perp \xi + E^+ \beta)\| + \lambda_2\|C(E^\perp \xi + E^+ \beta)\|$$

subject to $$\frac{\partial h_{I_i}}{\partial q} J_q(q)(E^\perp \xi + E^+ \beta) \geq \sigma_i, i = 1, \ldots, n_i$$

Where C is given by the equation above, λ1 and λ2 are chosen by weighting factors, $$J_D = \begin{bmatrix} J_H \\ E \\ C \end{bmatrix}^\perp.$$

And $\sigma_i$ is given by equation above.

Note that the minimization problem is strictly convex as the matrix $$\begin{bmatrix} J_H E^\perp \\ \lambda_1 C E^\perp \\ \lambda_2 J_D^T E^\perp \end{bmatrix}$$

is of full column rank. Therefore a unique solution always exists and may be efficiently found by using the gradient descent type of methods.

The following describes the equality and inequality constraints imposed on the system. We consider the two arms of the robot separately. Without loss of generality, consider only the left arm of the system. The kinematics as provided above given with $u \in R^9$ (7 for the arm and 2 for the motorized base), and $q \in R^{10}$. We focus only on user commanding the translation of the end-effector. Hence, $$J_H = J_t^p$$

the translational portion of $J_T$. The choice of the inequality and equality constraints is next described below.

1) Arm Workspace: There are two types of workspace constraints: joint limits and end-effector boundary constraint. The ranges of the joint angles are specified as follows (inequalities are interpreted component-wise):

$$\begin{bmatrix} -\pi/4 \\ -\pi/3 \\ -2\pi/3 \\ q_{4min} \\ -\pi/2 \\ -\pi/2 \\ -\pi/2 \end{bmatrix} \leq q_t \leq \begin{bmatrix} \pi/2 \\ \pi/3 \\ -\pi/4 \\ 2\pi/3 \\ \pi/2 \\ \pi/2 \\ \pi/2 \end{bmatrix}.$$

The values are provided by the manufacturer, except for $q_{4min}$ which is to be specified based on the distance between the current position of the motorized base to the target. When the motorized base is far from the target, the arm should bend close to the body while the motorized base moves forward (to avoid bumping into nearby objects). When the motorized base is close to the target, the arm can stretch to reach to forward. Thus, we let $q_{4min} = \pi/2$ (arm bent upward) when the distance between the motorized base 12 and target is larger than a threshold value (e.g., 1 m), and let $q_{4min} = 0$ (arm outstretched) when the distance is smaller than that threshold. The target location may either be specified by the user as the robot gets close, or detected automatically by the onboard cameras. To avoid self collision, we specify the coordinate of the end effector in x-direction, $$e_x^T p_{OT}$$

to be larger than 0.3 m. This is particularly important when the motorized base is backing up. Combining the above, we have 15 inequality constraints:

$$h_l = \begin{bmatrix} q_L - q_{L_{min}} \\ q_{L_{max}} - q_L \\ e_x^T p_{OT} - 0.3 \end{bmatrix}.$$

The corresponding Jacobian is $$J_l = \begin{bmatrix} I_7 & 0_{7\times 2} \\ -I_7 & 0_{7\times 2} \\ e_x^T J_{T_L}^p & 0_{7\times 2} \end{bmatrix}$$

where $$J_{T_L}^p$$

is the translational portion of the left arm end effector Jacobian, $J_{TL}$, $I_7$ is the 7×7 identity matrix. The parameters in the σ function are hand-tuned to be $\eta = \varepsilon = 0.15$ rad for the joint limit constraints, $\eta = 0.1$ m, $\varepsilon = 0.15$ m for the self collision constraint, c is set to 0.45 in all cases. In all cases except for $q_4$, the constraints are always satisfied, so we set $e_i$ to a small number 0.01. For $q_4$, the constraint region switches (due to $q_{4min}$), so the corresponding $e_i$ is chosen larger to be 0.1.

2) End-effector Orientation Control: To maintain the endeffector orientation at a specified configuration, we use a proportional feedback control kinematic control law:

$$\omega_T = -K_T q_v (R_{OT}^{des^T} R_{OT}),$$

where $$R_{OT}^{des} \text{ and } R_{OT}$$

are the desired and actual end-effector orientation matrix, $K_T$ is the feedback gain and $q_v$ is the vector quaternion. Thus, the first set of equality constraint is given with the corresponding Jacobian $$J_E = [J_{T_L}^R 0_{3\times 2}]$$

where $$J_{T_L}^R$$

is the rotational portion of the endeffector Jacobian $J_{TL}$.

3) Motorized base 12 Movement Constraint: As described, we impose an additional equality constraint to ensure the base follows the user commanded motion when the arm reaches the workspace boundary. In the component form, $$(-v_H^{(y)} p_{OT}^{(y)} - v_H^{(x)} p_{OT}^{(x)}) \omega_B + v_H^{(y)} v_B = 0$$

with the corresponding constraint Jacobian given by:

$$J_{EB} = [0_{1\times 7} - v_H^{(y)} p_{OT}^{(y)} - v_H^{(x)} p_{OT}^{(x)} v_H^{(y)}].$$

4) Obstacle Avoidance: Obstacles in the workspace may be detected by appropriate sensors, e.g., ultrasound range sensor, time-of-flight sensor, cameras, etc. In our current implementation, we use four IR sensors placed at the front side of the motorized base 12 to measure the distance of the obstacle ahead, $d_i$, i=1, . . . , 4. Suppose the minimum distance threshold for the sensors are $d_{i_{min}}$, i=1, . . . , 4. Then we have the inequality constraints $$h_I = [d_1 - d_{1_{min}} \, d_2 - d_{2_{min}} \, d_3 - d_{3_{min}} \, d_4 - d_{4_{min}}]^T.$$

The corresponding Jacobian is $$J_I = [0_{4\times 8}[-1,-1,-1,-1]^T]$$

since $$\dot{d}_i = -v_B$$

(forward velocity decreases the distance to obstacle). In order the forward moving velocity to decrease when the motorized base 12 is close to the obstacle, we set a relatively small value of c and large value of ε in σ, e.g., c=0.5, ε=1.2 m, so that the speed reduction starts at 1.2 m away from the obstacle. The size of the buffer zone is set to η=0.1 m, so the motorized base 12 starts to decelerate as far as 1.3 m from obstacle. Since we expect the inequality constraints always to be satisfied, $e_i$ is chosen as a small number, 0.01.

Figure 11:
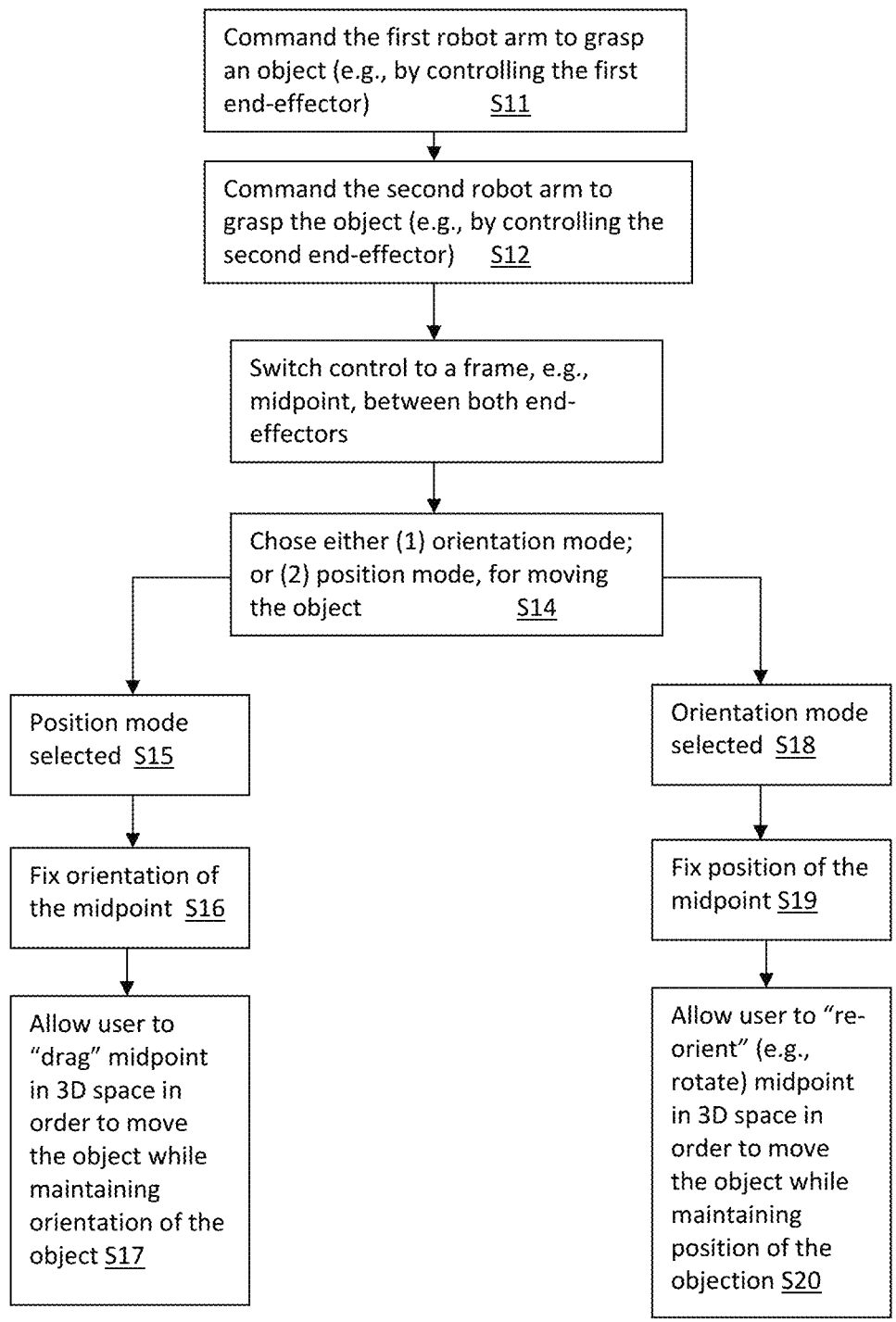
FIG. 11 depicts a computing infrastructure of the robotic assistant according to embodiments.

Referring now to FIG. 11, an illustrative control platform is shown in which laptop 26 is provided with a robot manager 58 that includes: (1) a set of communication interfaces 60 for communication with various systems, and (2) a control system 62 for interpreting commands and controlling the robotic assistant 10. In this example, robot manager 58 is adapted to receive remote interface commands 64 (e.g., from a Jamboxx) or Internet based commands 66 (e.g., from a health care provider). Whenever a command is received, it is interpreted by the control system 62 to move or control aspects of the robotic assistant 10. As shown, the robot manager 58 is capable of sending and receiving command signals to the motorized base 12, dual arm robot 16, sensors 68 or other devices 70. As noted, the motorized base 12 includes its own control platform having software for causing the motorized base 12 to move/respond according to received commands. The dual arm robot 16 likewise has its own unique control platform and software for causing its arms to move/respond. Because the control platforms for the two are distinct, each is controlled with unique input commands. In addition, sensors 68 and other devices 70 may also be controlled by the control system 62. The control system 62 includes a control algorithm 63, described above, for managing movements of the motorized base 12 and dual arm robot 16, based on inputs, constraints, etc.

Figure 12:
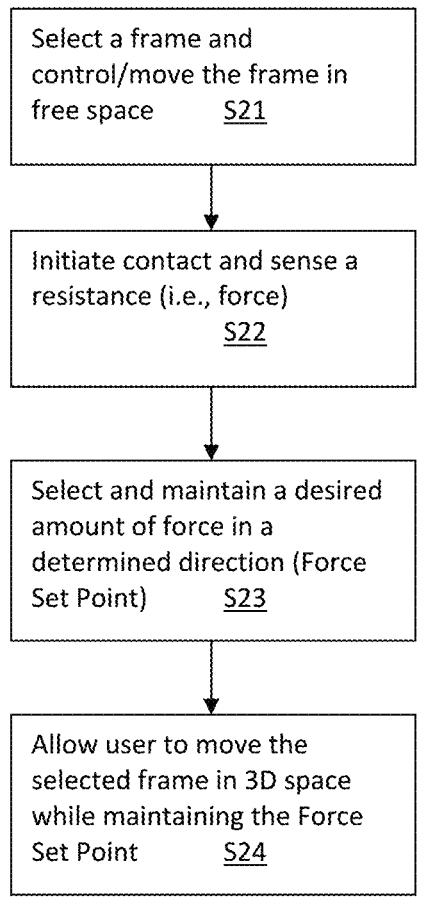
FIG. 12 depicts a flow diagram showing a process for operating the robotic assistant according to embodiments.

FIG. 12 depicts a generalized flow diagram showing a process for controlling the robotic assistant 10. At S1, the operator uses the input controller (e.g., Jamboxx) to select a frame of the robotic assistant to control. In one typical example, the operator would select an end effector, which is located proximate the grippers at the end of an arm. However, the operator may select other points, e.g., a wrist, shoulder, etc. Next at S2, the operator uses the input controller to command the selected frame to move within a three dimensional space. For example, the operator can use the Jamboxx to command the end effector to move towards an object on a table.

The process next determines at S3 if the selected arm is within the workspace, i.e., can the end effector reach a desired point without the need to move the motorized base. If no, the motorized base is moved within the workspace at S3, without yet moving the arm. Once the arm is in the workspace, a determination is made at S5 whether there are any constraints. For example, is there an object blocking the path, etc. If no, then the arm is independently moved as commanded by operator at S6. If yes, then the arm movement is limited or altered based on the constraint.

As will be appreciated, various aspects of the invention may be implemented as a computer program product stored on one or more computer readable storage mediums. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Python, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

An illustrative computing system may comprise any type of computing device and, and for example includes at least one processor (e.g., CPU 54 of FIG. 11), memory 52, an input/output (I/O) 56 (e.g., one or more I/O interfaces and/or devices), and a communications pathway. In general, processor(s) execute program code which is at least partially fixed in memory 52. While executing program code, processor(s) can process data, which can result in reading and/or writing transformed data from/to memory and/or I/O for further processing. The pathway provides a communications link between each of the components in computing system. I/O 56 can comprise one or more human I/O devices, which enable a user to interact with the computing system.

Furthermore, it is understood that the described algorithms or relevant components thereof (such as an API component) may also be automatically or semi-automatically deployed into a computer system by sending the components to a central server or a group of central servers. The components are then downloaded into a target computer that will execute the components. The components are then either detached to a directory or loaded into a directory that executes a program that detaches the components into a directory. Another alternative is to send the components directly to a directory on a client computer hard drive. When there are proxy servers, the process will, select the proxy server code, determine on which computers to place the proxy servers' code, transmit the proxy server code, then install the proxy server code on the proxy computer. The components will be transmitted to the proxy server and then it will be stored on the proxy server.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A robotic assistant, comprising:
   a motorized base having at least two motor driven wheels controlled by a first control platform;
   a dual arm robot mounted on the motorized base, the dual arm robot having a first arm and a second arm controlled by a second control platform;
   a remote sip and puff mouth controller having three degrees of operational input to allow a user to control an end effector of the dual arm robot within a three dimensional space; and
   a computer system that receives command signals from the remote sip and puff mouth controller to move the end effector, and includes a control system that translates the command signals into a first type of control signal for directing the motorized base to move, and a second type of control signal for directing the dual arm robot to move, wherein movement of the motorized base is realized without direct control from the user.

2. The robotic assistant of claim 1, wherein the motorized base comprises a retrofitted power wheelchair that includes a horizontally oriented adapter plate mounted thereon that is adapted to secure the dual arm robot.

3. The robotic assistant of claim 1, wherein the dual arm robot includes 14 degrees of operational freedom.

4. The robotic assistant of claim 1, wherein the command signals from the remote sip and puff mouth controller are communicated wirelessly.

5. The robotic assistant of claim 1, wherein the computer system includes a further input system for receiving command signals from a second source via the Internet.

6. The robotic assistant of claim 1, wherein control system includes an algorithm that instructs the motorized base to move only when both the first arm and the second arm are outside a defined workspace.

7. The robotic assistant of claim 6, wherein algorithm only instructs the first arm or second arm to move when the motorized base is not moving.

8. A control platform for controlling the operation of a robotic assistant, comprising:
   a control system that separately communicates with a motorized based and a dual arm robot mounted on the motorized base, wherein the control system implements a first type of control signal to control the motorized base, and a second type of control signal to control the dual arm robot;
   an input for receiving command signals from a remotely located controller, wherein the command signals include a proposed movement in a three dimensional space of an end effector associated with a selected arm of the dual arm robot; and
   a software algorithm that dictates the motion of the motorized base and dual arm robot based on the proposed movement, wherein the software algorithm only instructs the motorized base to move when the selected arm is outside a defined workspace, and only instructs the selected arm to move when the motorized base is stationary, and wherein movement of the motorized base is realized without direct control from the remotely located controller.

9. The control platform of claim 8, wherein the software algorithm limits movement of the selected arm based on existing constraints.

10. The control platform of claim 8, wherein the remotely located controller includes a device selected from a group consisting of: a sip and puff device, a tongue command device, an eye/blink tracker, and a joystick.

11. The control platform of claim 8, further comprising a second input for receiving remote commands via the Internet.

12. The control platform of claim 8, further separately communicates with at least one sensor.

13. The control platform of claim 8, wherein each arm of the dual arm robot includes seven degrees of movement, and wherein the software algorithm maps three degrees of operational input from the remotely located controller to the seven degrees of movement.

14. The control platform of claim 8, wherein proposed movement includes a velocity.

15. A robotic assistant, comprising:
- a motorized base having at least two motor driven wheels controlled by a first control platform;
- a dual arm robot mounted on the motorized base, the dual arm robot having a first arm and a second arm controlled by a second control platform;
- an input for receiving signals from a remotely located controller, the remotely located controller having three degrees of operational input for providing a proposed movement of an end effector of the robotic assistant; and
- a control system that separately communicates with the motorized based and dual arm robot, wherein the control system implements a first type of control signal to control the motorized base, and a second type of control signal to control the dual arm robot, and wherein the control system includes a software algorithm that dictates the motion of the motorized base and dual arm robot based on the proposed movement, wherein the software algorithm only instructs the motorized base to move when a selected arm is outside a defined workspace, and only instructs the selected arm to move when the motorized base is stationary, and wherein movement of the motorized base is realized without direct control from the remotely located controller.

16. The robotic assistant of claim 15, wherein the software algorithm limits movement of the selected arm based on existing constraints.

17. The robotic assistant of claim 15, wherein the remotely located controller includes a device selected from a group consisting of: a sip and puff device, a tongue command device, an eye/blink tracker, and a joystick.

18. The robotic assistant of claim 15, further comprising a second input for receiving remote commands via the Internet.

19. The robotic assistant of claim 15, wherein the control system separately communicates with at least one sensor.

20. The robotic assistant of claim 15, wherein each arm of the dual arm robot includes seven degrees of movement, and wherein the software algorithm maps three degrees of operational input from the remotely located controller to the seven degrees of movement.

21. The robotic assistant of claim 15, wherein proposed movement includes a velocity.

* * * * *